United States Patent
Sookraj et al.

(10) Patent No.: US 9,718,755 B2
(45) Date of Patent: Aug. 1, 2017

(54) METHODS FOR COPRODUCTION OF TEREPHTHALIC ACID AND STYRENE FROM ETHYLENE OXIDE

(71) Applicant: NOVOMER, INC., Waltham, MA (US)

(72) Inventors: Sadesh H. Sookraj, Waltham (ZA); Jay J Farmer, Ithaca, NY (US)

(73) Assignee: Novomer, Inc., Waltham, MA (US)

( * ) Notice: Subject to any disclaimer, the term of this patent is extended or adjusted under 35 U.S.C. 154(b) by 0 days.

(21) Appl. No.: 15/199,047

(22) Filed: Jun. 30, 2016

(65) Prior Publication Data

US 2017/0001939 A1   Jan. 5, 2017

Related U.S. Application Data

(60) Provisional application No. 62/187,334, filed on Jul. 1, 2015.

(51) Int. Cl.
   *C07C 51/14* (2006.01)

(52) U.S. Cl.
   CPC .................... *C07C 51/14* (2013.01)

(58) Field of Classification Search
   None
   See application file for complete search history.

(56) References Cited

U.S. PATENT DOCUMENTS

| | | | |
|---|---|---|---|
| 3,885,155 A | 5/1975 | Anbar | |
| 4,230,885 A | 10/1980 | Wu | |
| 4,427,884 A | 1/1984 | Anbar et al. | |
| 4,973,841 A | 11/1990 | Purser | |
| 5,438,194 A | 8/1995 | Koudijs et al. | |
| 5,661,299 A | 8/1997 | Purser | |
| 6,852,865 B2 | 2/2005 | Coates et al. | |
| 2002/0028909 A1 | 3/2002 | Kelsey et al. | |
| 2009/0246430 A1 | 10/2009 | Kriegel et al. | |
| 2011/0262669 A1 | 10/2011 | Kriegel et al. | |
| 2014/0197580 A1 | 7/2014 | Poulat | |
| 2015/0126772 A1 | 5/2015 | Cao et al. | |

FOREIGN PATENT DOCUMENTS

| | | |
|---|---|---|
| WO | WO 2009/155086 | 12/2009 |
| WO | WO 2010/118128 | 10/2010 |
| WO | WO 2012/030619 | 3/2012 |

(Continued)

OTHER PUBLICATIONS

Slowik, M. et al., "Catalytic; conversion of waste carbon monoxide to valuable chemicals & materials." Clean Technology, 2010, pp. 283-286. See p. 283; and figures 1, 2. Only pp. 283-284.

(Continued)

*Primary Examiner* — Sudhakar Katakam
*Assistant Examiner* — Jennifer C Sawyer
(74) *Attorney, Agent, or Firm* — Spence, PC

(57) ABSTRACT

The present invention provides methods for the production of terephthalic acid and derivatives thereof using ethylene oxide, carbon monoxide and furan as feedstocks. The process is characterized by high yields and high carbon efficiency. The process can utilize 100% biobased feedstocks (EO via ethanol, CO via biomass gasification, and furan via known processes from cellulosic feedstocks). In one aspect, processes of the invention coproduce biobased terephthalic acid and biobased styrene.

13 Claims, 3 Drawing Sheets

(56) References Cited

FOREIGN PATENT DOCUMENTS

| WO | WO 2013/063191 | 5/2013 |
| WO | WO 2013/122905 | 8/2013 |
| WO | WO 2013/126375 | 8/2013 |
| WO | WO 2014/004858 | 1/2014 |
| WO | WO 2014/008232 | 1/2014 |

OTHER PUBLICATIONS

Getzler Y. D. Y. L., "Catalytic carbonylation of beta-lactones to succinic anhydrides," Journal of the American Chemical Society, 2004, vol. 126, No. 22, pp. 6842-6843. See Table 1. Abstract only.
Vera, A. M. et al., "Synthesis and crystal structure of dimethyl-7-oxabicyclo[2.2.1] hept-5-ene exo,exo-2,3-dicarboxylate." Journal of Chemical Crystallography, 2007, vol. 37, pp. 543-548. See p. 544. Abstract Only.
Mahmoud, E. et al., "Production of benzoic acid from biomass-derived furan and methyl acrylate using lewis acidic zeolites," In Catalysis at the Confluence of Science and Technology, NAM24 Pittsburgh, PA, Jun. 15, 2015,pp. 1-2. See p. 1; and scheme 1.
Collias, D. I. et al., Biobased terephthalic acid technologies: I literature Review; Industrial Biotechnology, 2014, vol. 10, No. 2, p. 91-105. See whole document. Abstract Only.
Tachibana, Y. et al., "Synthesis and verification of biobased terephthalic acid from furfural." Scientific Reports, Feb. 4, 2015 (Offline), vol. 5, article No. 8249 (5 internal pages) See pp. 1, 2; and figure 1.

METHODS FOR COPRODUCTION OF TEREPHTHALIC ACID AND STYRENE FROM ETHYLENE OXIDE

CROSS REFERENCE TO RELATED APPLICATION

This application claims the benefit of U.S. Provisional Application 62/187,334 filed Jul. 1, 2015.

BACKGROUND OF THE INVENTION

Terephthalic acid (TPA) and its esters and derivatives are important precursors for the synthesis of polyesters and other useful materials.

The largest use of TPA at present is production of polyesters. For example, TPA is used to produce polyethylene terephthalate (PET) which is used extensively in consumer goods packaging, most prominently in the now ubiquitous plastic water bottles. TPA is produced on the scale of many millions of tons per year scale by oxidation of xylenes which are obtained from petroleum distillates.

There is strong demand from consumers and consumer goods companies for sustainable alternatives to petroleum-based plastics for packaging applications. Indeed, Coca Cola® and others have recently introduced PET containing biobased monoethylene glycol (MEG). Beverage bottles made from this PET are branded as the "Plant Bottle™" and have been well received in the marketplace. Unfortunately, since about 70% of the mass (and 80% of the carbon atoms) in PET derives from terephthalic and isophthalic acids, replacing petroleum-sourced MEG with biobased material yields PET that is only about 30% biobased and contains only 20% renewable carbon. There is huge interest in biobased IPA and TPA to enable fully biobased PET production, but to date no economically feasible biobased processes exist.

Polystyrene is another polymer that is derived from petroleum feedstocks and utilized on huge scale (billions of kgs per year). To make matters worse, polystyrene is not widely recycled and is therefore a large contributor to litter and landfill waste. At present there is no bio-based polystyrene available to consumer goods companies.

The present invention solves this problem and others related thereto.

SUMMARY OF THE INVENTION

The present invention addresses the problem that current biobased routes to terephthalic acid are carbon inefficient and expensive. The invention captures the recognition that terephthalic acid and related aromatic compounds can be accessed using ethylene oxide, carbon monoxide and furan as feedstocks. The process is characterized by high yields and high carbon efficiency. The process can utilize 100% biobased feedstocks (EO via ethanol, CO via biomass gasification, and furan via known processes from cellulosic feedstocks).

In addition, the invention provides access to biobased styrene that is derivable from biobased feedstocks and which can be efficiently produced as a co-product in an integrated facility for making biobased terephthalic acid.

The inventive processes have advantages relative to other proposed processes for biobased aromatic diacids in terms of cost and carbon efficiency. The inventive processes provide unprecedented flexibility in terms of the manufacturer's ability to modulate the bio-content of the product: the terephthalic acid produced by the process can contain 0, 2, 4, 6, or 8 biomass-derived carbon atoms. This flexibility allows TPA producers to leverage various combinations of biobased and fossil-based feedstocks (e.g. chosen on best combination of availability, cost, or carbon footprint of each material) to provide the market with cost-effective low carbon footprint chemicals and polymers.

In a first aspect, the present invention provides novel processes for the production of terephthalic acid (TPA) and derivatives thereof using furan, ethylene oxide and carbon monoxide as feedstocks.

In a second aspect, the present invention provides novel processes for the production of terephthalic acid (TPA) and derivatives thereof using furan, ethanol, and carbon monoxide as feedstocks.

In a third aspect, the present invention provides novel processes for the coproduction of styrene, terephthalic acid (TPA) and derivatives thereof using furan, ethanol, and carbon monoxide as feedstocks.

In certain embodiments, the invention provides processes for the integrated production of aromatic diacids from biomass, representative processes according to this embodiment include the steps of:

a) treating biomass to produce ethanol;
b) treating biomass to produce carbon monoxide;
c) converting the ethanol to ethylene oxide;
d) contacting ethylene oxide with the carbon monoxide in the presence of a catalyst to form beta propiolactone;
e) optionally converting the beta propiolactone to a product selected from the group consisting of acrylic acid, an acrylate ester, an acrylate salt and a combination of two or more of these;
f) contacting the beta propiolactone (or the product of step (e)) with furan to provide a product containing a cyclohexene ring;
g) dehydrating the cyclohexene ring-containing product to provide an aromatic compound selected from an aromatic carboxylic acid, a salt of an aromatic carboxylic acid; an ester of an aromatic acid; and a mixture of any two or more of these
h) treating the aromatic compound to disproportionate it into benzene and a product selected from the group consisting of: terephthalic acid, a mono- or di-ester of terephthalic acid, a mono- or bis-salt of terephthalic acid, and a mixture of any two or more of these.

DEFINITIONS

Figure 1:
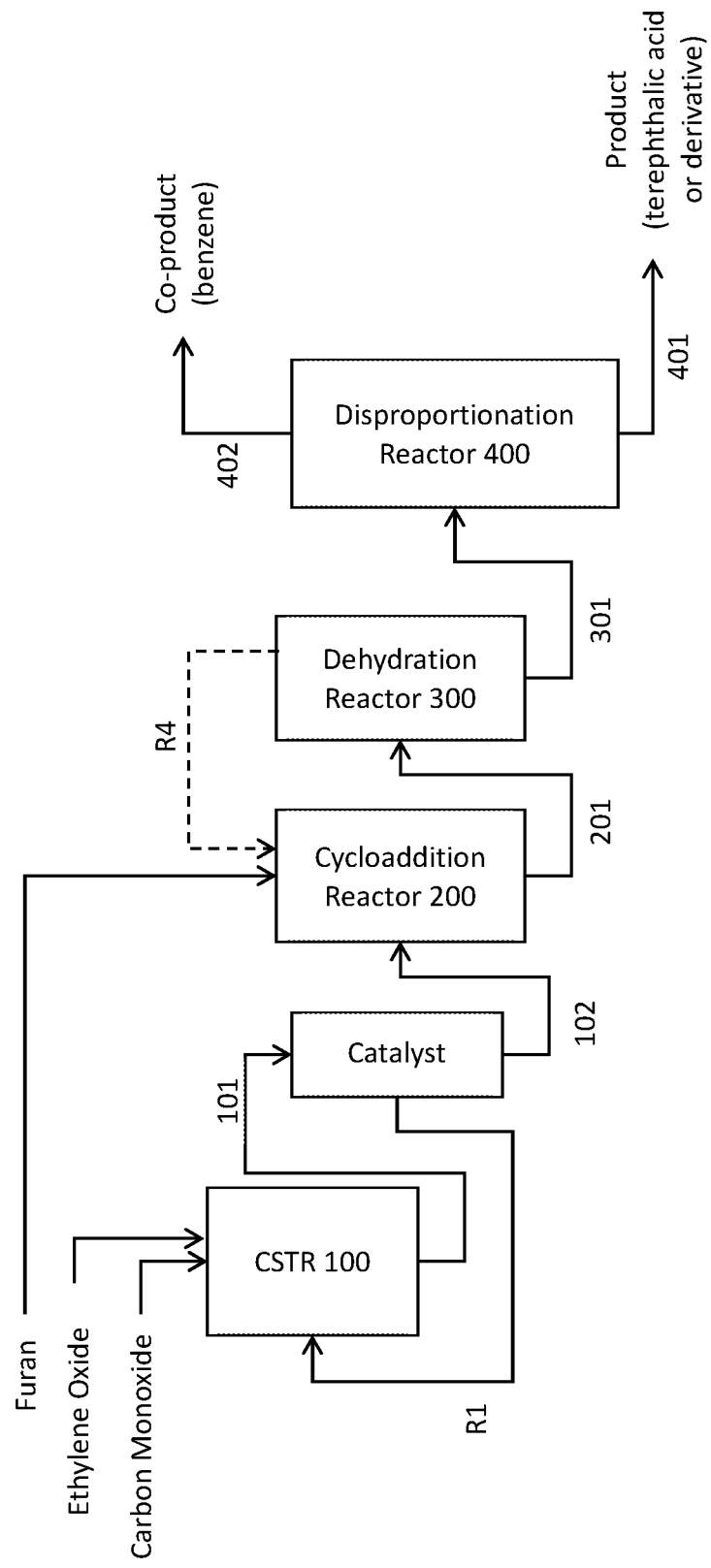
FIG. 1 is a flow diagram depicting various embodiments for the process arrangement of the invention.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March March's *Advanced Organic Chemistry*, 5th Edition, *John* Wiley & Sons, Inc., New York, 2001; Larock, Comprehensive *Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of enantiomers or diastereomers are provided.

Furthermore, certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In some embodiments the compound is made up of at least about 95%, 97%, 98%, 99%, 99.5%, 99.7%, 99.8%, or 99.9% by weight of an enantiomer. In some embodiments the enantiomeric excess of provided compounds is at least about 90%, 95%, 97%, 98%, 99%, 99.5%, 99.7%, 99.8%, or 99.9%. In some embodiments, enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "hetercyclyl," "heterocycloaliphatic," or "heterocyclic" groups.

The term "epoxide", as used herein, refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "glycidyl", as used herein, refers to an oxirane substituted with a hydroxyl methyl group or a derivative thereof. The term glycidyl as used herein is meant to include moieties having additional substitution on one or more of the carbon atoms of the oxirane ring or on the methylene group of the hydroxymethyl moiety, examples of such substitution may include, but are not limited to: alkyl groups, halogen atoms, aryl groups etc. The terms glycidyl ester, glycidyl acrylate, glydidyl ether etc. denote substitution at the oxygen atom of the above-mentioned hydroxymethyl group, i.e. that oxygen atom is bonded to an acyl group, an acrylate group, or an alkyl group respectively.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer of the present invention is a copolymer, terpolymer, heteropolymer, block copolymer, or tapered heteropolymer of one or more epoxides.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include cyclopropane, cyclobutane, cyclopentane, cyclohexane, bicyclo[2,2,1]heptane, norbornene, phenyl, cyclohexene, naphthalene, spiro[4.5] decane, The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)N(R^\circ)_2$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}S(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-8}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur, or, notwithstanding the definition above, two independent occurrences of $R^\circ$, taken together with their intervening atom(s), form a 3-12-membered saturated, partially unsaturated, or aryl mono- or polycyclic ring having 0-4 heteroatoms independently selected from nitrogen, oxygen, and sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —O(haloR$^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-4}C(O)N(R^\circ)_2$; —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)OR$^\bullet$, or —SSR$^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*_2$, =NNHC(O)R*, =NNHC(O)OR*, =$NNHS(O)_2R^*$, =NR*, =NOR*, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —$R^\bullet$, -(haloR$^\bullet$), —OH, —OR$^\bullet$, —O(haloR$^\bullet$), —CN, —C(O)OH, —C(O)OR$^\bullet$, —$NH_2$, —NHR$^\bullet$, —NR$^\bullet_2$, or —$NO_2$, wherein each R$^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "catalyst" refers to a substance the presence of which increases the rate of a chemical reaction, while not being consumed or undergoing a permanent chemical change itself.

As used herein, the term "about" preceding one or more numerical values means the numerical value ±5%.

DETAILED DESCRIPTION OF THE INVENTION

Processes

In one aspect, the present invention encompasses novel processes for the production of terephthalic acid and derivatives thereof.

In certain embodiments, the process utilizes ethylene oxide, furan and carbon monoxide as the feedstocks. In certain embodiments, the ethylene oxide is derived from ethanol via ethylene; therefore in another aspect, the present invention provides a process for the conversion of ethanol, carbon monoxide and furan into terephthalic acid and derivatives thereof. In certain embodiments, any one or more of the furan, the ethanol, or the carbon monoxide is derived from biomass.

In certain embodiments, the processes comprise reacting the ethylene oxide and carbon monoxide to form beta propiolactone (BPL).

In another aspect, the present invention encompasses processes for the efficient production of benzoic acid based on the reaction of furan with BPL. In certain embodiments, the inventive processes operate in a continuous flow format. In certain embodiments the process includes continuously passing a mixture of furan (or a derivative thereof) and beta propiolactone through a reaction zone, optionally in the presence of solvent, catalysts, or co-reactants.

In certain embodiments, subsequent dehydration of the addition product of the furan with the BPL is performed in a continuous flow format. In certain embodiments, reaction of the furan and BPL occurs in a first fixed bed reactor and the effluent from the reactor is fed to a second reactor where the product is heated under dehydrative conditions to effect aromatization of the addition product.

In another aspect, the invention encompasses processes for the production of benzoic acid and/or terephthalic acid that are integrated with an ethylene oxide-based process for BPL production. In certain embodiments, the ethylene oxide-based process produces BPL continuously and a stream from that process is fed to a continuous reactor where it is contacted with furan. In certain embodiments, the resulting product is fed to an aromatization reactor where it is converted to an aromatic acid. In certain embodiments, the process includes a disproportionation reactor for conversion of benzoic acid to terephthalic acid. In certain embodiments, the disproportionation process co-produces benzene.

In certain embodiments, the processes include an optional step of converting the beta propiolactone to acrylic acid, or a salt or ester of acrylic acid. This product is then contacted with the furan to form a seven carbon product containing a cyclohexene ring.

It should be noted here that the term "seven carbon product" as used in this specification refers to a product where the seven carbon atoms are joined to each other through carbon-carbon bonds—it should be understood that such a product may contain a total of more than seven carbon atoms if one includes carbon atoms separated from the seven carbon core by one or more bonds through heteroatoms. For example, if a reactant in this step were butyl acrylate, the seven carbon product could contain a total of eleven carbon atoms: i.e. the seven carbon atoms in the substituted cyclohexene product core derived from the four carbon atoms in the furan and the three carbon atoms of the acrylate moiety, plus four additional carbon atoms in the form of the butyl group in the ester (if that ester remains intact through the process). The butyl group is separated from the seven carbon core by an oxygen atom and therefore is not counted.

In certain embodiments, the processes include the step of dehydrating the seven carbon product containing a cyclohexene ring to form a product comprising a substituted benzene ring.

In certain embodiments, the processes include the step of disproportionating the product comprising a substituted benzene ring to provide benzene and a product selected from the group consisting of: terephthalic acid, a mono or diester of terephthalic aid, a mono or bis metal salt of terephthalic acid; and a mixture of any two or more of these.

In certain embodiments, the benzene produced by the disproportionation is further converted to a useful monomer such as styrene.

Therefore, in certain embodiments a process is provided for the conversion of ethylene oxide, furan and carbon monoxide to terephthalic acid or a derivative thereof, the process comprising the steps of:

a) reacting the ethylene oxide and carbon monoxide to form beta propiolactone;

b) converting the beta propiolactone to an unsaturated compound selected from the group consisting of: acrylic acid, an ester of acrylic acid, a salt of acrylic acid, and a mixture of any two or more of these;

c) reacting the unsaturated compound from step (b) with the furan to provide a seven carbon product containing a cyclohexene ring;

d) dehydrating the seven carbon product containing a cyclohexene ring to form a product comprising a substituted benzene ring; and e) disproportionating the product comprising a substituted benzene ring to provide two product streams: a first product stream comprising a product selected from the group consisting of: terephthalic acid, a mono or diester of terephthalic aid, a mono or bis metal salt of terephthalic acid; and a mixture of any two or more of these and a second product stream comprising benzene.

In certain embodiments a process is provided for the conversion of ethylene oxide, furan and carbon monoxide to terephthalic acid or a derivative thereof, the process comprising the steps of:

a) reacting the ethylene oxide and carbon monoxide to form beta propiolactone;

b) reacting the beta propiolactone with the furan to provide a seven carbon product containing a cyclohexene ring;

c) dehydrating the seven carbon product containing a cyclohexene ring to form a product comprising a substituted benzene ring; and d) disproportionating the product comprising a substituted benzene ring to provide two product streams: a first product stream comprising a product selected from the group consisting of: terephthalic acid, a mono or diester of terephthalic aid, a mono or bis metal salt of terephthalic acid; and a mixture of any two or more of these and a second product stream comprising benzene.

In other embodiments, the present invention provides processes for the formation of terephthalic acid from ethanol, carbon monoxide and furan. These processes have the advantage of utilizing three operational feedstocks that are among the most abundant and efficiently produced of all biobased chemicals. As such the inventive processes have substantial advantages in terms of cost and overall carbon efficiency compared to alternative routes to biobased terephthalic acid or biobased styrene.

In certain embodiments, a process is provided for the conversion of ethanol, carbon monoxide and furan to terephthalic acid, the process comprising the steps of:

a) reacting ethanol in a dehydration reactor to provide ethylene;

b) reacting the ethylene with oxygen to provide ethylene oxide;

c) reacting the ethylene oxide with carbon monoxide to provide beta propiolactone;

d) converting this beta propiolactone to an unsaturated compound selected from the group consisting of: acrylic acid, an ester of acrylic acid, a salt of acrylic acid, and a mixture of any two or more of these;

e) reacting the unsaturated compound from step (d) with the furan to provide a seven carbon product containing a cyclohexene ring;

f) dehydrating the seven carbon product containing a cyclohexene ring to form a product comprising a substituted benzene ring; and g) disproportionating the product comprising a substituted benzene ring to provide two product streams: a first product stream comprising a product selected from the group consisting of: terephthalic acid, a mono or diester of terephthalic aid, a mono or bis metal salt of terephthalic acid; and a mixture of any two or more of these and a second product stream comprising benzene.

In certain embodiments, a process is provided for the conversion of ethanol, carbon monoxide and furan to terephthalic acid, the process comprising the steps of:

a) reacting ethanol in a dehydration reactor to provide ethylene;

b) reacting the ethylene with oxygen to provide ethylene oxide;

c) reacting the ethylene oxide with carbon monoxide to provide beta propiolactone;

d) reacting the beta propiolactone with the furan to provide a seven carbon product containing a cyclohexene ring;

e) dehydrating the seven carbon product containing a cyclohexene ring to form a product comprising a substituted benzene ring; and f) disproportionating the product comprising a substituted benzene ring to provide two product streams: a first product stream comprising a product selected from the group consisting of: terephthalic acid, a mono or diester of terephthalic aid, a mono or bis metal salt of terephthalic acid; and a mixture of any two or more of these, and a second product stream comprising benzene.

In certain embodiments of processes where the beta propiolactone is converted to an unsaturated compound before being reacted with the furan, the unsaturated compound comprises acrylic acid. The process of converting beta propiolactone to acrylic acid can be any of those known in the art, including but not limited to: reaction of the beta lactone with water or an alcohol in the presence of an acid, polymerization of the beta propiolactone to polypropiolactone followed by thermal cracking of the polymer, thermolysis of the propiolactone in the presence of a nucleophile or other similar processes.

In certain embodiments of processes where the beta propiolactone is converted to an unsaturated compound before being reacted with the furan, the unsaturated compound comprises an ester of acrylic acid. No particular limits are placed on the identity of the ester produced in this process. The optimal choice will depend on the price and availability of the alcohol, and the ease with which the alcohol can be recovered from the process and re-used. Suitable esters include those derived from lower aliphatic alcohols (for example, $C_{1-8}$ alcohols), and aromatic alcohols (for example benzyl alcohol). Such esters can be formed by any traditional means. In certain embodiments, the acrylate ester is formed from acrylic acid which is derived from beta propiolactone as described in the preceding paragraph. In other embodiments, the acrylate ester is formed directly from the beta propiolactone—for example, by contacting the beta propiolactone with a suitable alcohol under dehydrating conditions.

In certain embodiments of processes where the beta propiolactone is converted to an unsaturated compound before being reacted with the furan, the unsaturated compound comprises a salt of acrylic acid. Such acrylate salts can comprise any suitable cation. Suitable cations include metal cations (for example group I or group II metal cations) or organic cations such as ammonium or phosphonium cations. The acrylate salts can be formed by any traditional means. In certain embodiments, the salt is formed from acrylic acid which is derived from beta propiolactone as described above. In other embodiments, the acrylate salt is formed directly from the beta propiolactone—for example, by contacting the lactone with the hydroxide salt of a Group I metal.

In certain embodiments, the beta propiolactone is formed from reaction of the ethylene oxide and one molar equivalent of carbon monoxide in the presence of a carbonylation catalyst. In certain embodiments the carbonylation is performed in a continuous process, for example in a continuous stirred tank reactor. Suitable carbonylation catalysts and process conditions for this reaction are disclosed in U.S. Pat. No. 6,852,865 and in published PCT applications WO 2010118128, WO 2013063191, and WO 2014008232 the entire content of each of which is incorporated herein by reference.

In certain embodiments, the reaction of ethylene oxide with carbon monoxide is catalyzed by a cobalt-based catalyst. In certain embodiments, the reaction of ethylene oxide with carbon monoxide is catalyzed by a catalyst comprising a cobalt carbonyl compound in combination with a Lewis acid. In certain embodiments the Lewis acid is a cationic metal-centered Lewis acid and the cobalt carbonyl is an anionic species.

In certain embodiments, the reaction of ethylene oxide with carbon monoxide is performed at a superatmospheric pressure. In certain embodiments, the reaction of ethylene oxide with carbon monoxide is performed at a pressure from about 150 psi to about 3000 psi. In certain embodiments, the reaction pressure is between 200 psi and 1000 psi, between 400 and 800 psi, between 800 and 1200 psi, or between 1200 and 2000 psi.

In certain embodiments, the reaction of ethylene oxide with carbon monoxide is performed in a continuous process using a homogenous carbonylation catalyst which is separated from the beta propiolactone product and returned to the carbonylation process. In certain embodiments, the reaction of ethylene oxide with carbon monoxide is performed continuously in the presence of a heterogeneous carbonylation catalyst.

In certain embodiments, the reaction of ethylene oxide with carbon monoxide is performed in a solvent. In certain embodiments, the solvent comprises an ether. In certain embodiments, the solvent is selected from the group consisting of 1,4-dioxane, tetrahydrofuran, glyme, diglyme, triglyme, tetraglyme, and t-butyl methyl ether. In certain embodiments, the reaction of ethylene oxide with carbon monoxide is performed in a solvent comprising diglyme. In certain embodiments, the reaction of ethylene oxide with carbon monoxide is performed in a solvent comprising tetrahydrofuran.

In certain embodiments of these processes, the seven carbon product containing a cyclohexene ring formed from the reaction with furan comprises an oxo-bridged cyclohexene ring. In certain embodiments, the oxo-bridge is located between the two allylic carbons adjacent to the double bond in the cyclohexene ring (e.g. between ring carbons 3 and 6 if the double bond carbons are numbered 1 and 2). In certain embodiments, the seven carbon product further comprises a substituent at a homoallylic position of the cyclohexene ring (e.g. the cyclohexene ring has a substituent at carbon 4 or 5 if the double bond carbons are numbered 1 and 2). In certain embodiments, the homoallylic substituent is selected from the group consisting of: carboxy, carboxy ester, and carboxylate salt.

In certain embodiments, the reaction of the furan with beta propiolactone provides a 7-Oxabicyclo[2.2.1]hept-5-ene-2-carboxylic acid having a structure:

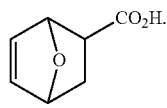

In certain embodiments, the reaction of the furan with beta propiolactone comprises a formal 2-plus-4 cycloaddition reaction where the two methylene carbons of the lactone ring react as an olefin would. Without being bound by theory, or thereby limiting the scope of the claimed invention, it is believed that under the cycloaddition conditions, the beta lactone may undergo rearrangement to form acrylic acid (or an acrylate ester if an alcohol is present or an acrylate salt if a base is present) which then undergoes cycloaddition in a separate reaction. On the other hand, it is also possible that the propiolactone reacts with directly with the furan in a concerted fashion.

In certain embodiments, the reaction of beta propiolactone with furan is promoted by heating a mixture of the furan and the beta propiolactone. In certain embodiments, the cycloaddition reaction is promoted by contacting a mixture of the furan and the beta propiolactone with a catalyst. In certain embodiments, the cycloaddition reaction is promoted by contacting a mixture of the furan and the beta propiolactone with a Lewis acid catalyst. In certain embodiments, the cycloaddition reaction is conducted in a solvent. In certain embodiments, the cycloaddition reaction is conducted in the gas phase. In certain embodiments, the cycloaddition reaction is conducted in the presence of a solid catalyst. In certain embodiments, the cycloaddition reaction is conducted in by heating a mixture of the furan and the beta propiolactone in the presence of a solid Lewis acid catalyst. In certain embodiments, the cycloaddition reaction is conducted in by heating a mixture of the furan and the beta propiolactone in a solvent in the presence of a solid Lewis acid catalyst. In certain embodiments, the cycloaddition step of comprises continuously flowing the mixture of furan and the beta propiolactone through a plug flow reactor containing a solid Lewis acid catalyst. In certain embodiments, the cycloaddition reaction is conducted in by heating a mixture of the furan and beta propiolactone in a solvent in the presence of a homogeneous Lewis acid catalyst. In certain embodiments, the cycloaddition reaction is conducted in by heating a mixture of the furan and the beta propiolactone in a solvent in the presence of a homogeneous Lewis acid catalyst in a continuous stirred tank reactor. In certain embodiments, the cycloaddition reaction is conducted in by flowing a mixture of the furan and the beta propiolactone through a plug flow reactor in a solvent in the presence of a homogeneous Lewis acid catalyst. In certain embodiments, the cycloaddition reaction is conducted at a controlled temperature to retard the retro cycloaddition reaction of the desired product. In certain embodiments, the cycloaddition reaction is conducted at a temperature below about 100° C. In certain embodiments, the cycloaddition reaction is conducted at a temperature below about 90° C., below about 80° C., below about 75° C., below about 70° C., below about 65° C., below about 60° C., below about 50° C., or below about 40° C.

In certain embodiments, the reaction between beta propiolactone and furan is promoted by heating a mixture of the furan and the beta propiolactone. In certain embodiments, the cycloaddition reaction is conducted in by flowing a mixture of the furan and the beta propiolactone through a heated plug flow reactor in a solvent in the absence of a catalyst. In certain embodiments, a mixture of beta propiolactone and furan is heated to a temperature between 50° C. and 300° C. In certain embodiments, the mixture is heated to a temperature between 50° C. and 150° C., between 100° C. and 200° C., between 120° C. and 180° C. or between 150° C. and 220° C. In certain embodiments, the step of heating the mixture of the furan and the unsaturated compound comprises flowing the mixture through a heated plug flow reactor. In certain embodiments, acrylic acid and unreacted furan are present in the outlet of the heated reactor. In certain embodiments, one or both of acrylic acid or furan present in the outlet of the reactor are recycled to the inlet for further reaction.

In certain embodiments, the beta propiolactone is first converted to an unsaturated compound selected from: acrylic acid, and acrylate ester, and an acrylate salt, and the furan is subsequently reacted with the unsaturated compound. In certain embodiments, the cycloaddition reaction is promoted by heating a mixture of the furan and the unsaturated compound. In certain embodiments, the mixture is heated to a temperature between 50° C. and 300° C. In certain embodiments, the mixture is heated to a temperature between 50° C. and 150° C., between 100° C. and 200° C., between 120° C. and 180° C. or between 150° C. and 220° C. In certain embodiments, the step of heating the mixture of the furan and the unsaturated compound comprises flowing the mixture through a heated plug flow reactor. In certain embodiments, the step of heating the mixture of the furan and the unsaturated compound comprises flowing the mixture through a heated plug flow reactor in the presence of a catalyst. In certain embodiments, the step of heating the mixture of the furan and the unsaturated compound comprises flowing the mixture through a heated plug flow reactor in the absence of a catalyst.

In certain embodiments, the reaction of the furan with the unsaturated compound comprises a 2-plus-4 cycloaddition reaction. In certain embodiments, the cycloaddition reaction is promoted by contacting a mixture of the furan and the unsaturated compound with a catalyst. In certain embodiments, the cycloaddition reaction is promoted by contacting a mixture of the furan and the unsaturated compound with a Lewis acid catalyst. In certain embodiments, the cycloaddition reaction is conducted in a solvent. In certain embodiments, the cycloaddition reaction is conducted in the gas phase. In certain embodiments, the cycloaddition reaction is conducted in the presence of a solid catalyst. In certain embodiments, the cycloaddition reaction is conducted in by heating a mixture of the furan and the unsaturated compound in the presence of a solid Lewis acid catalyst. In certain embodiments, the cycloaddition reaction is conducted in by heating a mixture of the furan and the unsaturated compound in a solvent in the presence of a solid Lewis acid catalyst. In certain embodiments, the cycloaddition step of comprises continuously flowing the mixture of furan and the unsaturated compound through a plug flow reactor containing a solid Lewis acid catalyst. In certain embodiments, the cycloaddition reaction is conducted in by heating a mixture of the furan and the unsaturated compound in a solvent in the presence of a homogeneous Lewis acid catalyst. In certain embodiments, the cycloaddition reaction is conducted in by heating a mixture of the furan and the unsaturated compound in a solvent in the presence of a homogeneous Lewis acid catalyst in a continuous stirred tank reactor. In certain embodiments, the cycloaddition reaction is conducted in by flowing a mixture of the furan and the unsaturated compound through a plug flow reactor in a solvent in the presence of a homogeneous Lewis acid catalyst. In certain embodiments, the cycloaddition reaction is conducted at a controlled temperature to retard the retro cycloaddition reaction. In certain embodiments, the cycloaddition reaction is conducted at a temperature below about 100° C. In certain embodiments, the cycloaddition reaction is conducted at a temperature below about 90° C., below about 80° C., below about 75° C., below about 70° C., below about 65° C., below about 60° C., below about 50° C., or below about 40° C.

In certain embodiments, the step of dehydrating the cyclohexene ring-containing compound comprises heating the cyclohexene compound in the presence of a dehydrating agent. In certain embodiments, the step includes continuously removing water vapor from a reaction zone where the dehydration reaction is performed. In certain embodiments, the dehydration reaction is acid catalyzed. In certain embodiments, the dehydration reaction is acid catalyzed by phosphoric or sulfuric acid. In certain embodiments, the dehydration reaction is acid catalyzed. In certain embodiments, the dehydration reaction is acid catalyzed by a solid supported acid catalyst. In certain embodiments, the dehydration reaction is performed by heating the cyclohexene ring-containing compound in the presence of sulfuric acid. In certain embodiments, the dehydration reaction is performed by heating the cyclohexene ring-containing compound in the presence of sulfonic acid resin. In certain embodiments where the cyclohexene ring-containing compound comprises an ester, the dehydration step results in hydrolysis of the ester group. In certain embodiments where the cyclohexene ring-containing compound comprises an ester, the dehydration conditions promote ester hydrolysis and the product is an acid. In certain embodiments, where the cyclohexene ring-containing compound is an acid or an ester, the dehydration step results in formation a carboxylate salt.

In certain embodiments, the dehydration reaction is catalyzed by reaction with a strong base. In certain embodiments, where the cyclohexene compound comprises a substituent that is a carboxylate ester, the dehydration reaction comprises treating the ester with a strong base in the presence of water to form a salt of an aromatic acid. In certain embodiments, the salt formed comprises potassium benzoate. In certain embodiments, the potassium benzoate from the dehydration step is continuously fed to the disproportionation reaction. In certain embodiments, the alcohol liberated by the ester hydrolysis is recovered and used to generate additional acrylate ester from beta propiolactone or acrylic acid formed during an earlier step in the process.

In certain embodiments, the retro cycloaddition of the cyclohexene compound occurs to some extent during the dehydration reaction. Therefore, in certain embodiments, furan and acrylic acid (or an ester or salt of acrylic acid) are formed in the dehydration reactor. In certain embodiments, the process includes the step of recovering one or more of these materials and feeding them to back to the input of the cycloaddition reactor. In this manner, the overall selectivity of the process is kept high even where the selectivity in the dehydration step may not be optimal.

In certain embodiments, the product of the dehydration reaction comprises benzoic acid, a salt of benzoic acid, an ester of benzoic acid, benzoic anhydride or a mixture of any two or more of these. In certain embodiments, the product of the dehydration reaction comprises benzoic acid. In certain embodiments, the product of the dehydration reaction comprises a compound selected from the group consisting of: methyl benzoate, ethyl benzoate, butyl benzoate, 2-ethylhexylbenzoate, a benzoic ester of a $C_{3-12}$ alcohol, and a mixture of any two or more of these. In certain embodiments, the product of the dehydration reaction comprises potassium benzoate. In certain embodiments, the product of the dehydration reaction comprises sodium benzoate. In certain embodiments, the product of the dehydration reaction comprises benzoic acid anhydride.

In certain embodiments, the step of disproportionating the substituted aromatic compound formed in the dehydration step comprises treating a feed stream comprising a monosubstituted benzene compound with a catalyst at elevated temperature to form a product mixture containing disubstituted benzene compounds along with benzene. In certain embodiments, the disubstituted benzene compounds comprise terephthalic acid, isophthalic acid, phthalic acid or derivatives thereof (such as esters, salts or anhydrides). In certain embodiments, the disubstituted benzene product contains a preponderance of terephthalic acid (or derivatives thereof) and lesser amounts of isophthalic or phthalic acids (or their derivatives). In certain embodiments, terephthalic acid (or its derivatives) comprise at least 80% of the diacids produced. In certain embodiments, terephthalic acid (or its derivatives) comprise at least 85%, at least 90%, at least 95%, or at least 97% of the diacids produced. In certain embodiments, terephthalic acid (or its derivatives) comprises essentially the only diacid produced.

In certain embodiments, the step of disproportionating the monosubstituted benzene compound comprises converting benzoic acid to a metal benzoate salt and then treating the salt with a suitable catalyst. In certain embodiments, the step of contacting with a catalyst is performed at an elevated temperature. In certain embodiments, the step of contacting the benzoate salt is performed at a temperature above about 200° C., above about 250° C., above about 300° C., above about 350° C. or above about 400° C. In certain embodiments, the step of contacting the benzoate salt is performed at elevated pressure. In certain embodiments, the step of contacting the benzoate salt is performed at elevated pressure under an atmosphere of $CO_2$.

In certain embodiments, the step of disproportionating the monosubstituted aromatic compound comprises continuously flowing a feed stream comprising a monosubstituted benzene compounds over a heterogeneous a catalyst at elevated temperature to form a product mixture containing para disubstituted benzene compounds. In certain embodiments, the reaction zone is heated. In certain embodiments, the reaction zone is heated to a temperature between 100° C. and 500° C. In certain embodiments, the reaction zone is heated to a temperature between 100° C. and 200° C., between 120° C. and 180° C., between 150° C. and 220° C., between 200° C. and 300° C., or between 300° C. and 450° C.

In certain embodiments, the catalyst utilized for the disproportionation comprises a transition metal. In certain embodiments, the disproportionation is performed in the presence of a catalyst comprising a Group 10-12 transition metal. In certain embodiments, the disproportionation is performed in the presence of a catalyst comprising a Group 12 transition metal. In certain embodiments, the disproportionation is performed in the presence of a catalyst comprising cadmium. In certain embodiments, the disproportionation is performed in the presence of a catalyst comprising zinc. In certain embodiments, the disproportionation is performed in the presence of a catalyst comprising mercury.

In certain embodiments, the process further includes continuously withdrawing a product stream containing terephthalic acid or an ester or salt thereof from the disproportionation reaction zone. In certain embodiments, the process further includes a step of purifying the terephthalic acid (or salts or esters thereof) withdrawn from the reaction zone. In certain embodiments, the purification includes distillation, extraction, crystallization, or a combination of both of these.

In certain embodiments, the process further includes continuously withdrawing a co-product stream containing benzene from the disproportionation reaction zone. In certain embodiments, the process further includes a step of purifying the benzene withdrawn from the reaction zone. In certain embodiments, the purification includes distillation, extraction, crystallization or combinations of these.

In certain embodiments, the benzene co-product from the disproportionation reaction is treated to convert it to styrene. This transformation is readily accomplished using known processes, for example, by reaction of the benzene with ethylene to produce ethyl benzene which is then oxidatively dehydrogenated to provide styrene. In certain embodiments, where either or both of the ethylene oxide and furan feeds to the process are derived from biomass, the resulting benzene contains 2, 4, or 6 biobased carbon atoms. This product can be reacted with ethylene derived from bio ethanol to provide biobased styrene thereby providing an opportunity to make biobased polystyrene and related products. The styrene thereby produced may contain 2, 4, 6, or 8 biobased carbon atoms. In certain embodiments, the styrene produced has the novel attribute of containing four carbon atoms derived from ethanol. The integrated process to biobased terephthalic acid and styrene is remarkably carbon efficient since each step is high yielding and every carbon atom in the feedstocks is incorporated into useful final products.

In certain embodiments, where the process is integrated to ethanol production, both the ethylene oxide feedstock, and the ethylene needed to convert the benzene co-product to styrene are derived from the same ethanol production process.

In certain embodiments, processes of the present invention are characterized in that they are continuous processes. In certain embodiments, such continuous processes are characterized in that two or more of the steps described above are combined and performed without isolation and purification of intermediate products or, in some cases, two or more reactions are efficiently combined in a single operation or reactor.

In certain embodiments, the steps of converting beta propiolactone to acrylic acid (or an acrylate ester or salt) and cycloaddition reaction with furan are performed in a single reactor. In certain embodiments, the steps of performing the cycloaddition reaction and dehydrating the cycloaddition product are combined. In certain embodiments, the steps of dehydrating the cycloaddition product and disproportionating the monosubstituted benzene product to terephthalic acid or a derivative thereof are combined.

In certain embodiments, processes of the present invention are characterized in that the terephthalic acid produced is biobased. Each of the three feedstocks may be derived from biobased feedstocks or derived from traditional fossil sources. One advantage of the present processes is the ability to independently select the source of each of the three feedstocks. For example, in certain parts of the world, furan (primarily derived from cellulosic waste) is abundant but access to biobased ethylene oxide is limited. In such regions the inventive processes described herein can be utilized to manufacture terephthalic acid with significant biocontent which is still cost-effective. Likewise, other regions may have abundant access to bio-sourced carbon monoxide (e.g. from gasification of biomass or municipal solid waste) but limited access to biobased ethylene oxide or furan.

In certain embodiments, the present invention is characterized by high carbon efficiency. The term carbon efficiency in this context refers to the fraction of carbon atoms in the primary process feedstocks (e.g. furan, ethylene oxide and carbon monoxide) that are incorporated into the final products (e.g. terephthalic acid and benzene). For example, if the process consumes 1 kg of ethylene oxide (containing 46 moles of carbon), 0.6 kg of carbon monoxide (containing 23 moles of carbon) and 1.8 kg of furan (containing 106 moles of carbon) to produce 1.6 kg of terephthalic acid (containing 77 moles of carbon), and 0.8 kg of benzene (containing 62 moles of carbon) the carbon efficiency of the process would be calculated to be approximately 79%.

In certain embodiments the present invention encompasses processes for the production of terephthalic acid and benzene from ethylene oxide, furan and carbon monoxide, characterized in that the carbon efficiency to terephthalic acid and benzene from the ethylene oxide, furan and carbon monoxide feedstocks is greater than 70%. In certain embodiments the processes of the present invention are characterized in that the carbon efficiency is greater than 75%, greater than 77%, greater than 78%, greater than 79%, greater than 80%, greater than 81%, greater than 82%, greater than 83%, greater than 84%, or greater than 85%.

In certain embodiments the present invention encompasses processes for the production of terephthalic acid and styrene from ethanol, furan and carbon monoxide, characterized in that the carbon efficiency to terephthalic acid and styrene from the ethanol, furan and carbon monoxide feedstocks is greater than 65%. In certain embodiments the processes of the present invention are characterized in that the carbon efficiency is greater than 67.5%, greater than 70%, greater than 75%, greater than 77%, greater than 78%, greater than 80%, greater than 81%, greater than 82%, greater than 83%, or greater than 85%.

EXAMPLES

The following examples describe processes according to the principles described herein.

Example 1: Continuous Process for Production of Terephthalic Acid and Benzene from Ethylene Oxide, Carbon Monoxide and Furan This example features the combination of a continuous carbonylation process wherein the carbonylation stage is operated at steady state in a continuous stirred tank reactor (CSTR) to produce a beta propiolactone stream which is fed directly to a cycloaddition reactor where it is reacted with furan to produce 7-oxabicyclo[2.2.1]hept-5-ene-2-carboxylic acid. This material is fed to a dehydration unit to produce benzoic acid and water and the benzoic acid is disproportionated to produce terephthalic acid and benzene. With reference to FIG. 1:

Carbonylation reaction zone comprising continuous stirred tank reactor CSTR 100 is fed with ethylene oxide, solvent (diglyme) and carbon monoxide. In the reactor, the ethylene oxide is contacted with carbon monoxide at 1000 psi pressure in the presence of a carbonylation catalyst thereby producing beta propiolactone.

Carbonylation product stream 101 comprising solvent, dissolved carbonylation catalyst, and 20 wt % beta propiolactone is taken from CSTR 100 and directed to catalyst separator 100b consisting of a nanofiltration membrane unit where the beta propiolactone and solvent permeate through a nanofiltration membrane while dissolved catalyst is retained in a retentate stream and returned to CSTR 100 via recycling stream R1.

The beta propiolactone stream 102 is continuously fed to Cycloaddition Reactor 200 where it is combined with furan in a 1:1 mol ratio. The furan and beta propiolactone react over a molecular sieve-supported zirconium-based catalyst to form the cycloaddition product compound 7-oxabicyclo[2.2.1]hept-5-ene-2-carboxylic acid. Product stream 201 containing the cycloaddition product exits the cycloaddition reactor.

Product stream 201 is continuously fed to Dehydration Reactor 300 where the 7-oxabicyclo[2.2.1]hept-5-ene-2-carboxylic acid contained in stream 201 is contacted with sulfuric acid with continuous removal of water vapor and thereby converted to benzoic acid which exits via product stream 301.

Benzoic acid stream 301 is fed to Disproportionation Reactor 400 where the benzoic acid is converted to a mixture of terephthalic acid and benzene. In Disproportionation Reactor 400 the benzoic acid is first converted to its potassium salt and is then contacted at elevated temperature with a cadmium-containing catalyst. Stream 401 exiting Disproportionation Reactor 400 is treated to recover the desired terephthalic acid via product stream 401 while the coproduced benzene is removed by stream 402.

Example 1a

The process of Example 1a is operated according to the principles described above in Example 1 except that after catalyst separator unit 200b a distillation is performed on stream 102 to separate the solvent from the beta propiolactone. The solvent is returned to CSTR 100, while the neat beta propiolactone stream is fed to cycloaddition reactor 200.

Example 1b

The process of Example 1b is operated according to the principles described above in Example 1 except that furan and acrylic acid residues created by retro-cycloaddition side-reactions in Dehydration Reactor 300 are recovered and returned to Cycloaddition Reactor 200 via recycle stream R4.

Example 1c

The process of Example 1c is operated according to the principles described above in Example 1 except that the furan and beta propiolactone are reacted by flowing them through a heated plug flow reactor in the absence of a catalyst. A recycle loop is provided to return furan, unreacted beta propiolactone, and/or acrylic acid to the reaction zone for further conversion.

Example 1d

The process of Example 1d is operated according to the principles described above in Example 1 except that Dehydration Reactor 300 comprises a plug flow reactor containing a solid strong acid resin as a catalyst.

Example 1e

The process of Example 1e is operated according to the principles described above in Example 1d except that after Dehydration Reactor 300 a crystallizer is used to separate benzoic acid from unreacted 7-oxabicyclo[2.2.1]hept-5-ene-2-carboxylic acid. The unreacted substrate is recycle to the inlet of the plug flow reactor 300.

Figure 2:
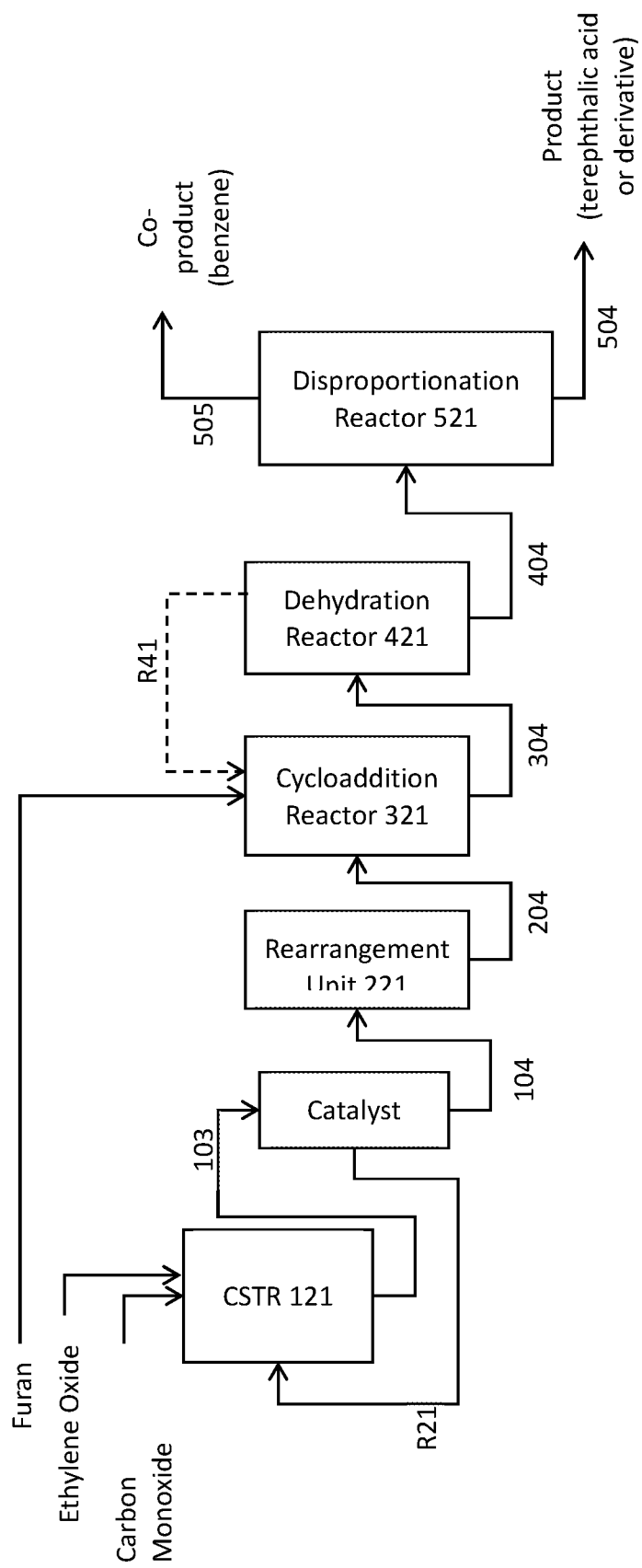
FIG. 2 is a flow diagram depicting variations in the embodiments for the process arrangement of the invention shown in FIG. 1.

Example 2: Alternate Continuous Process for Production of Terephthalic Acid and Benzene from Ethylene Oxide, Carbon Monoxide and Furan This example features the combination of continuous carbonylation process wherein the carbonylation stage is operated at steady state in a continuous stirred tank reactor (CSTR) to produce a beta propiolactone stream which is fed to a rearrangement reactor where it is converted to acrylic acid. The acrylic acid is fed to a cycloaddition reactor where it is reacted with furan to produce 7-oxabicyclo[2.2.1]hept-5-ene-2-carboxylic acid. This material is fed to a dehydration stage to produce benzoic acid and water and the benzoic acid is disproportionate to produce terephthalic acid and benzene. With reference to FIG. 2:

Carbonylation reaction zone comprising a continuous stirred tank reactor CSTR 121 is fed with ethylene oxide and carbon monoxide. In the reactor, the ethylene oxide is contacted with carbon monoxide at superatmospheric pressure in the presence of a carbonylation catalyst producing beta propiolactone.

Carbonylation product stream 104 comprising beta propiolactone, solvent, dissolved carbonylation catalyst and a fraction of unreacted ethylene oxide is taken from CSTR 121 and directed to Catalyst Separator 121b consisting of a nanofiltration unit where beta propiolactone and solvent permeate through a membrane while carbonylation catalyst is retained in the reaction medium and returned to CSTR 121 via recycling stream R21.

The beta propiolactone stream 104 is continuously fed to Rearrangement Unit 221 where the lactone is polymerized to produce polypropiolactone which is continuously fed to a thermolysis zone and converted to acrylic acid vapor which exits by stream 204.

The acrylic acid stream 204 is continuously fed to Cycloaddition Reactor 321 where it is combined with furan in a 1:1 mol ratio. The furan and acrylic acid react over a solid-supported Lewis acid catalyst (for example a tin or zirconium based molecular sieve-supported catalyst) to form a cycloaddition product. Product stream 304 exiting the cycloaddition reactor contains the cyclohexene compound 7-oxabicyclo[2.2.1]hept-5-ene-2-carboxylic acid.

Product stream 304 is continuously fed to Dehydration Reactor 421 where the 7-oxabicyclo[2.2.1]hept-5-ene-2-carboxylic acid contained in stream 304 is converted to benzoic acid which exits via product stream 404.

Stream 404 is fed to Disproportionation Reactor 521 where the benzoic acid in stream 404 is converted to a mixture of terephthalic acid and benzene. In Disproportionation Reactor 521 the benzoic acid is converted to its potassium salt which is then contacted at elevated temperature with a cadmium-containing catalyst. Stream 504 exiting Disproportionation Reactor 521 is treated to recover the terephthalic acid via product stream 504 while the coproduced benzene is removed by stream 505.

Example 2a

The process of Example 2a is operated according to the principles described above in Example 2 except that after catalyst separator unit 121b a distillation is performed on stream 104 to separate the solvent from the beta propiolactone. The solvent is returned to CSTR 121, while the neat beta propiolactone stream is fed to Rearrangement Reactor 221.

Example 2b

The process of Example 2b is operated according to the principles described above in Example 2 except that furan and acrylic acid residues created by retro-cycloaddition side-reactions in Dehydration Reactor 421 are recovered and returned to Cycloaddition Reactor 321 via recycle stream R41.

Example 2c

The process of Example 2c is operated according to the principles described above in Example 2 except that in the Rearrangement Unit 221, the beta propiolactone is contacted with ethanol and the rearrangement product exiting in stream 204 comprises ethyl acrylate.

The ethyl acrylate in stream 204 is fed to Cycloaddition Reactor 321 for reaction with furan to produce the ethyl ester of 7-oxabicyclo[2.2.1]hept-5-ene-2-carboxylic acid. This ester removed in stream 304 and fed to Dehydration Reactor 421 where it is converted to ethyl benzoate. The ethyl benzoate is fed via stream 404 to Disproportionation Reactor 521 where the ester is cleaved during conversion to potassium benzoate. The ethanol is recovered and fed back to Rearrangement Unit 221.

Example 3

A continuous process for production of terephthalic acid and styrene production from biomass.

Figure 3:
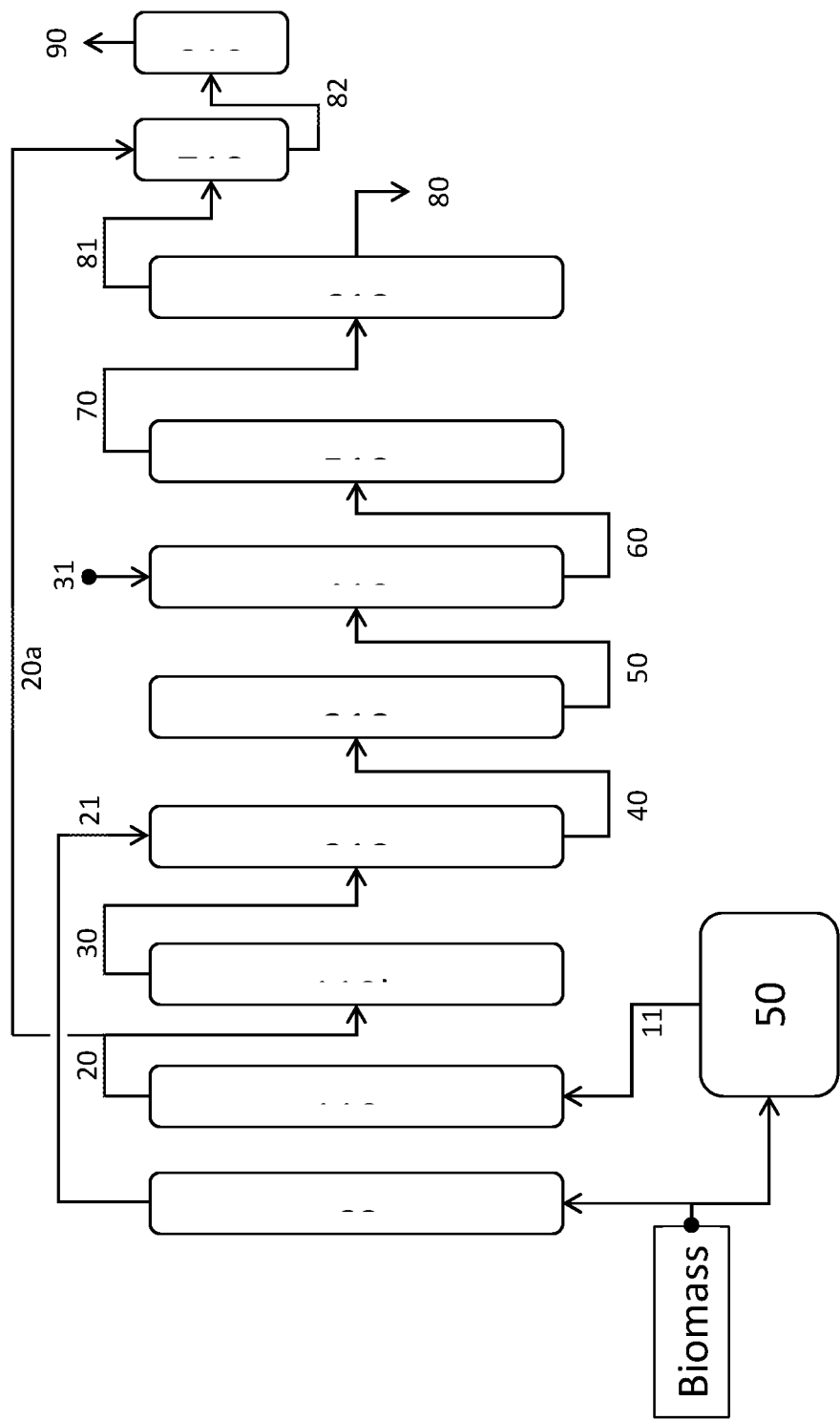
FIG. 3 is a flow diagram depicting various embodiment for an alternate flow arrangement for the process of this invention.

This example features a continuous process wherein ethanol, carbon monoxide and furan derived from biomass are the operational feedstocks and the process coproduces biobased styrene and terephthalic acid. With reference to FIG. 3:

Biomass suitable for fermentation is fed to fermentor 50 while lower grade biomass material is sent to gasifier 60. Ethanol from fermentor 50 is taken by stream 11 to dehydration reactor 110a which produces ethylene stream 20.

Ethylene oxide production unit 110b is fed with ethylene stream 20 and operates according to known principles to convert the ethylene to ethylene oxide in the presence of oxygen. Ethylene oxide exits unit 110b via stream 30.

Ethylene oxide stream 30 is fed to carbonylation stage 210 along with carbon monoxide stream 21 derived from biomass gasifier 60. In carbonylation stage 210, a homogeneous carbonylation catalyst promotes the reaction of carbon monoxide and ethylene oxide in a solvent using a continuous stirred tank reactor. Catalyst is separated from the product beta propiolactone solution by nanofiltration and recycled to the CSTR while solvent is removed from the beta propiolactone by distillation. Neat beta propiolactone exits stage 210 in stream 40.

Beta propiolactone stream 40 is directed to rearrangement reactor 310 where it is polymerized to polypropiolactone and heated to liberate acrylic acid vapor. The acrylic acid is recovered via product stream 50.

Product stream 50 is directed to reactor 410 where it is combined with furan entering from stream 31. In reactor 410 the furan and acrylic acid to produce 7-oxabicyclo[2.2.1] hept-5-ene-2-carboxylic acid which is taken from the reactor in product stream 60.

Stream 60 is fed to reactor 510 where the compound is treated under dehydrating conditions to produce benzoic acid and water. The benzoic acid exits reactor 510 via stream 70.

Benzoic acid stream 70 is fed to disproportionation unit 610 where it is converted to its potassium salt and treated with a catalyst to provide dipotassium terephthalate and benzene. The dipotassium terephthalate is converted to terephthalic acid and taken as product stream 80 while the benzene is removed via stream 81.

Benzene in stream 81 is directed to ethyl benzene unit 710 where it is contacted with ethylene from dehydration reactor 110a provided via stream 20a. Ethyl benzene exits unit 710 in stream 82 and is fed to dehydration unit 810. Biobased styrene exits unit 810 via stream 90.

Example 3a

The process of Example 3a is operated according to the principles described above in Example 3 except rearrangement reactor 310 is removed and neat beta propiolactone is fed directly to cycloaddition reactor 410.

Example 3b

The process of Example 3b is operated according to the principles described above in Example 3 except the beta propiolactone in stream 40 is contacted with n butanol under dehydrating conditions in reactor 310. Product stream 50 in this example contains n-butyl acrylate.

The n-butyl acrylate in stream 50 is fed to cycloaddition reactor 410 where it is contacted with furan from feed stream 31 and converted to n-butyl ester of 7-oxabicyclo[2.2.1]hept-5-ene-2-carboxylic acid which exits via stream 60 to dehydration reactor 510. In this example, the product exiting reactor 510 via stream 70 is n-butyl benzoate. In unit 610, the n-butyl benzoate is converted to potassium benzoate, the n-butanol liberated is recycled to rearrangement reactor 310.

Example 3c

The process of Example 3c is operated according to the principles described above in Example 3 except cycloaddition reactor 410 and dehydration reactor 510 are combined into one unit. In this Example the combined cycloaddition/dehydration reactor is operated with dual catalyst zones: a first catalyst zone containing a catalyst that promotes 2+4 cylcoaddition and a second catalyst zone containing a catalyst that promotes dehydration of oxabicyclo[2.2.1]hept-5-ene-2-carboxylic acid to benzoic acid. A degree of retro 2+4 cycloaddition occurs in the second catalyst zone such that the intermediate product stream from that zone contains a mixture of benzoic acid, acrylic acid and furan. The benzoic acid is separated from the acrylic acid and furan which are returned to the first catalyst zone for reconversion.

Example 3d

The process of Example 3d is operated according to the principles described above in Example 3 except reactor 410 contains a solid-supported Lewis acid catalyst (for example a tin or zirconium based molecular sieve-supported catalyst) and reactor 410 is operated at a temperature below about 80° C. to prevent retro cycloaddition reactions.

OTHER EMBODIMENTS

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A process for production of a chemical product comprising terephthalic acid or terephthalate by utilizing furan, ethylene oxide, and carbon monoxide as the feedstocks, the process comprising the steps of:
   reacting the ethylene oxide and carbon monoxide to form beta propiolactone; and
   deriving the chemical product from the beta propiolactone wherein the chemical product comprises at least one of terephthalic acid, a mono or diester of terephthalic aid, and a mono or bis metal salt of terephthalic acid.

2. The process of claim 1 wherein the carbon efficiency of the process is greater than 80%.

3. The process of claim 2, comprising the step of:
   converting the beta propiolactone to an unsaturated compound selected from the group consisting of: acrylic acid, an ester of acrylic acid an acrylate salt and a mixture of any two or more of these and deriving the chemical product from the unsaturated compound.

4. The process of claim 3, comprising the step of reacting the unsaturated compound with the furan to provide a seven carbon compound containing a cyclohexene ring and deriving the chemical product from the seven carbon compound.

5. The process of claim 4, further comprising the step of dehydrating the seven carbon compound to provide a compound containing a mono-substituted benzene ring and disproportionating the compound containing the mono-substituted benzene ring to produce at least a portion of the chemical product.

6. The process of claim 5, wherein the disproportionation of the mono-substituted benzene co-produces benzene.

7. The process of claim 1, characterized in that two adjacent ring carbon atoms in the benzene ring of the chemical product are derived from the ethylene oxide.

8. The process of claim 1, wherein at least one of the carbon monoxide; the ethylene oxide and the furan is biobased.

9. The process of claim 1, wherein, beta propiolactone is reacted with the furan to provide 7-Oxabicyclo[2.2.1]hept-5-ene-2-carboxylic acid having a structure:

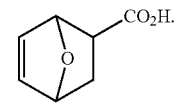

10. A process for production of a chemical product comprising terephthalic acid or terephthalate by utilizing furan, ethylene oxide, and carbonmonoxide as the feedstocks, the process comprising the steps of:
    reacting the ethylene oxide and carbon monoxide to form beta propiolactone;
    converting the beta propiolactone to an unsaturated compound selected from the group consisting of: acrylic acid, an ester of acrylic acid an acrylate salt;
    reacting the unsaturated compound with the furan to provide a seven carbon compound containing a cyclohexene ring;
    dehydrating the seven carbon compound to provide a compound containing a mono-substituted benzene ring; and
    disproportionating the compound containing the mono-substituted benzene ring to produce the chemical product wherein the chemical product comprises at least one of terephthalic acid, a mono or diester of terephthalic aid, and a mono or bis metal salt of terephthalic acid.

11. The process of claim 10, wherein the carbon efficiency of the process is greater than 80%.

12. The process of claim 10, characterized in that two adjacent ring carbon atoms in the benzene ring of the chemical product are derived from the ethylene oxide.

13. The process of claim 10, wherein at least one of the carbon monoxide; the ethylene oxide and the furan is biobased.

* * * * *